United States Patent [19]

Michaels

[11] Patent Number: 4,717,658

[45] Date of Patent: Jan. 5, 1988

[54] GRAM NEGATIVE BACTERIA SCREENING METHOD WITH HORSESHOE CRAB AMEBOCYTE LYSATE (LAL)

[75] Inventor: Angela A. Michaels, Elkhart, Ind.

[73] Assignee: Miles Inc., Elkhart, Ind.

[21] Appl. No.: 803,963

[22] Filed: Dec. 3, 1985

[51] Int. Cl.$^4$ .......................................... G01N 33/579
[52] U.S. Cl. ....................................... 435/19; 435/4; 436/502
[58] Field of Search ...................... 436/502; 435/4, 19

[56] References Cited

U.S. PATENT DOCUMENTS

| | | | |
|---|---|---|---|
| 4,188,264 | 2/1980 | Iwanaga | 436/502 |
| 4,276,050 | 6/1981 | Firca | 436/502 |
| 4,301,245 | 11/1981 | Lindsay | 436/502 X |

FOREIGN PATENT DOCUMENTS 68290  6/1979  Japan .

OTHER PUBLICATIONS

Chemical Abstracts, I, 102: 1464r (1985).
Chemical Abstracts, II, 102: 180282z (1985).

*Primary Examiner*—Sidney Marantz
*Attorney, Agent, or Firm*—Roger N. Coe

[57] ABSTRACT

A screening method for the determination of $10^4$ gram negative bacteria per milliliter of an undiluted urine sample and a unitary screening test device for the determination of at least $10^5$ gram negative bacteria per milliliter of an undiluted urine sample. The method and test device make use of Limulus amebocyte lysate (LAL) and a synthetic substrate containing a chromogenic or fluorogenic leaving group capable of being cleaved by activated lysate. This screening method and unitary screening device provide a quick, convenient, inexpensive indication of the possible presence of a urinary tract infection caused by gram negative bacteria.

16 Claims, 2 Drawing Figures

GRAM NEGATIVE BACTERIA SCREENING METHOD WITH HORSESHOE CRAB AMEBOCYTE LYSATE (LAL)

FIELD OF THE INVENTION

The invention relates to diagnostic test methods for screening urine samples for gram negative bacteria and to a unitary solid state test device useful for the same purpose.

UTILITY

The expression "gram negative bacteruria" is used to refer to urinary tract infections of gram negative etiology. Urinary tract infections are classified into four categories on the basis of symptoms, recurrence and complicating factors. Acute uncomplicated gram negative bacteruria may disappear spontaneously, but is usually followed by persistent or recurrent bacteruria which may require prolonged drug therapy. The three other categories of bacteruria, if untreated, may lead to kidney infection or death. In addition, while gram negative bacteruria is widespread and debilitating, the associated symptomology may be difficult to distinguish, producing a class of so-called asymptomatic patients.

While a culture of a urine sample can detect concentrations of $10^4$ bacteria per milliliter of sample, a concentration sometimes used as the cut off for normal gram negative bacteria content, culture results are not available for at least 18 to 24 hours, require trained personnel and are expensive to obtain. Microscopic examination is quicker, requiring approximately 45 minutes, but is sensitive to only $10^5$ bacteria per milliliter and also requires the use of trained personnel. Neither method could be considered a screening method. A screening method which is quick, convenient and inexpensive would be particularly useful for large scale testing in a population segment such as school children or armed forces personnel.

INFORMATION DISCLOSURE

The Limulus Amebocyte Lysate (LAL) assay is based on the use of a lysate derived from a natural material extracted from certain species of crab. It has recently been found that the lysate contains proenzymes and a natural substrate coagulogen. The lysate cascade is activated by endotoxin, a component of the cell wall of gram negative bacteria. The activation of the cascade results naturally in the formation of a gel endpoint.

A device consisting of a transparent tube containing reagents for the gelation LAL assay has been disclosed for the determination of endotoxin in EP-0-121-868. Any specimen liquid can be analyzed.

The presence of endotoxin in urine has also been related to the presence of bacteruria with instruments which can detect the turbidity resulting from the activation of the Limulus Amebocyte Lysate enzyme cascade by endotoxin. The extent of turbiditiy after the activation of the cascade by endotoxin is measured and has been related to the presence of bacteruria. The detection limit is reported to be $10^5$ bacteria per milliliter of sample. However, due to the high cost of the instrumentation required, this method cannot be considered a screening method.

Recently, synthetic peptide substrates containing chromogenic or fluorogenic groups, which can be cleaved by the clotting enzyme produced when the LAL cascade is activated by endotoxin, have become available. A variety of synthetic substrates have been disclosed. See, for example, Great Britain Pat. No. 1,547,747 and U.S. Pat. No. 4,188,264. In general, the two amino acid sequence, glycine-arginine, has been found to be critical for cleavage of a chromogenic or fluorogenic leaving group by the clotting enzyme. Cleavable leaving groups such as nitrophenyl, methylcoumarin derivatives, p(N,N-diethylamino)aniline and indoxyl have been disclosed. Japanese Pat. No. 56,42597 discloses the measurement of endotoxin in any body fluid, including urine, with a substrate whose cleavage product can react with 1-naphthol-2-sulfonic acid to provide a blue color.

Chromogenic or fluorogenic substrates have been used principally in assays for endotoxin in intravenous solutions and in blood. Measurements in blood have been related to bacteremia (bacterial infection in blood). Endotoxin determination in blood is complicated by the presence of inhibitors of the LAL cascade. Most patents and literature sources are directed either toward the elimination of these interfering factors or toward new synthetic substrates. See, for example, EP Patent Application No. 0-80-649, directed toward the removal of interferants required to measure endotoxin. The specification mentions the application of the disclosed method for removing interferants to a determination of bacteruria.

Japanese Patent Application 56-35994 discloses a device for the determination of endotoxin which contains a part having an enzyme precursor which has been separated from the lysate and a part having an optically measurable peptide substrate sealed in a separate container.

A chromogenic LAL solution assay has been disclosed (Nachum and Berzofsky, J. Clin. Microbiology, 759-763, 1985) for the determination of $10^5$ gram negative bacteria cells per milliliter for the diagnosis of gram negative bacteruria using the Whittaker, M.A., Bioproducts, Walkeville, MD kit (QCL-1000).

This invention provides a convenient screening method for the determination of $10^4$ gram negative bacteria per mL of an undiluted urine sample and a solid state test device sensitive to $10^5$ bacteria per milliliter urine sample.

DESCRIPTION OF THE DRAWINGS

The dotted line shows the reflectance of the test device immediately after contact (time=0). The dashed lines show the reflectance 45 and 90 seconds later. The solid lines, which overlap, show the reflectance between 135 and 225 seconds. The percent reflectance from the device decreases as the amount of color increases. FIG. 1 shows that stable color is reached in 135 seconds (approximately 2 mintues). The graph reflects the results of Example 3.

FIG. 2 is a graph showing reflectance data collected with a unitary solid state device. percent reflectance at 405 nm is expressed as K/S, where K is the absorption coefficient and S is the scattering coefficient. The calculation of K/S from %R was done with the Kubelka-Munk equation. The value of K/S increases as the amount of color developed in the device increases. K/S is plotted against time (t) in seconds. After incubation of the contacted test device for 7 minutes at 37 degrees Centigrade, reflectance at 405 nanometers was followed for 6 minutes. The unitary test device was prepared by pretreating paper with Gantrez® AN 119 available from GAF Corp., New York, N.Y. and impregnating the pretreated paper with lysate from Associates of Cape Cod, buffer and a commercially available p-nitroanilide substrate, The strips were dipped in saline bacteria solutions. The solid lines in FIG. 2 indicate negative bacteria content; the dashed lines indicate $10^5$ E. coli per milliliter and the dotted line indicates $10^6$ E. coli per milliliter. Dramatic increases in K/S or color are exhibited by the strips dipped in the latter samples. FIG. 2 shows that a unitary test device can provide differential results between negative samples and those containing $10^5$ gram negative bacteria. The graph reflects the results of Example 4.

SUMMARY OF THE INVENTION

The invention provides a screening method for the determination of at least $10^4$ gram negative bacteria per milliliter of a urine sample, a unitary test device for the determination of at least $10^5$ gram negative bacteria per milliliter urine sample, a method for preparing the device and a method for its use.

The screening method for determining the presence of at least $10^4$ gram negative bacteria per milliliter of a urine sample, comprises the steps of: (a) adding the undiluted urine sample to a test tube containing horseshoe crab amebocyte lysate, and a first buffer capable of resisting a pH change in the pH range of from about 6.3 to about 7.5 to form a test tube mixture, wherein the concentration of lysate is at least 3.5 milligrams per milliliter of test tube mixture formed; (b) incubating the test tube mixture for a time sufficient to activate the lysate; (c) contacting a test device with the activated test tube mixture, the test device comprising a carrier matrix incorporated with a second buffer capable of resisting a pH change in the pH range of from about 8.0 to about 8.9 and a synthetic peptide substrate containing a chromogenic or fluorogenic leaving group capable of being cleaved by the lysate; (d) removing the contacted test device; and (e) determining the concentration of the cleaved leaving group. The screening method is convenient, inexpensive and has sufficient sensitivity to detect concentrations of $10^4$ gram negative bacteria per milliliter urine sample, a concentration which is considered clinically significant but is often found in asymptomatic patients.

The invention also provides a unitary solid state test device for the determination of at least $10^5$ gram negative bacteria in a urine sample. The unitary solid state gram negative bacteruria screening device comprises a carrier matrix and a test composition incorporated therewith, the test composition comprising horseshoe crab amebocyte lysate, a divalent cation, a synthetic peptide substrate including a chromogenic or fluorogenic leaving group capable of being cleaved by the lysate, a buffer component capable of resisting a pH change in the pH range of from about 7.5 to about 8.5 and a stabilizing component capable of stabilizing the lysate. The unitary solid state test device is a particularly convenient format for screening large population groups and has a sensitivity equivalent to more expensive, time consuming formats now on the market.

DETAILED DESCRIPTION OF THE INVENTION

Because bacteruria is so prevalent in the population, many methods have been developed to detect and diagnose its presence. Presently no screening method is available for bacteruria which is sensitive to the presence to $10^4$ bacteria per milliliter of an undiluted urine sample using the LAL cascade with a synthetic substrate. Neither is there available a solid state unitary test device suitable for detecting the presence of at least $10^5$ gram negative bacteria per milliliter undiluted urine sample utilizing the LAL cascade with a synthetic substrate.

The assay for the detection of bacteruria is based on the natural enzyme cascade present in horseshoe crab amebocyte lysate. Horseshoe crab amebocyte lysate can be obtained from the Limulus or the Tachypleus species of crab. The Limulus species is the western species of horseshoe crab and Limulus lysate is readily available from Associates of Cape Cod, Woods Hole, MA. This is a preferred source of lysate since it has been found to be of consistent quality and is available in a concentrated form useful in the invention. Although the lysate cascade had been believed to be too sensitive to the presence of endotoxin to provide a useful test for bacteruria, the invention provides two formats carefully designed to give a positive indication of the presence of a threshold concentration of gram negative bacteria in a urine sample, a concentration considered to be an indication of a gram negative bacteria infection of the urinary tract.

A. Normal Concentrations of Endotoxin in Urine

To be useful, a screening method must provide a positive indication of a threshold concentration of an analyte which signals a possible medical problem, without giving an unacceptably high number of false positive tests. Usually a follow-up procedure is required after a positive result with a screening method. Therefore the usefulness of a screening method lies in its ability to provide a quick, convenient, low cost method of determining when more expensive tests should be performed. For bacteruria, a successful screening method must provide a positive indication of a desired concentration of gram negative bacteria per milliliter of urine sample without giving a false positive indication when only a normal concentration of such bacteria is present.

Although both instrumental turbidity measurements and gram staining have a sensitivity of $10^5$ cells per milliliter, some medical authorities believe that detection of $10^4$ cells per milliliter would pinpoint some asymptomatic patients or patients for whom the symptomology is difficult to assign to bacteruria. These patients could be helped in the early stages of bacterial infection but can be missed with presently available screening methods such as nitrite reagent strips which detect the presence of nitrate-reducing bacteria (a class of gram negative bacteria) or leukocyte reagent strips which detect leukocytes produced by the body due to an infection.

Nachum and Berzofsky, J. Clin. Microbiology, 759–763, 1985, found that normal urines can contain up to 20 nanograms per milliliter free endotoxin, a concentration which would indicate the presence of $10^3$ gram negative bacteria per milliliter. Results with the gelation assay support these findings. This background does not affect either the test tube/test device method of applicant's invention or the unitary test device format. The test tube/test device format is carried out under conditions that make it insensitive to those endotoxin levels. The unitary test device does not detect free endotoxin.

B. Test Tube/Test Device Method

This invention provides a screening method for bacteruria, sensitive to $10^4$ bacteria per milliliter of an undiluted urine sample. The method comprises adding the undiluted urine sample to a test tube containing lysate and a first buffer, mixing and incubating the mixture for a time sufficient to activate the lysate to the presence of $10^4$ gram negative bacteria cells per milliliter sample. The formation of the clotting enzyme by the LAL cascade after contact with endotoxin is referred to herein as activation. A test device, comprising a carrier matrix incorporated with a second buffer and a synthetic peptide substrate, is contacted with the activated test tube mixture. The test device is then removed and the detectable response of the device is determined. Synthetic substrates containing flurogenic or chromogenic leaving groups can be used. However, the preferred detectable response is color, as the result of the test can then be determined either visually or instrumentally by reflectance.

By controlling the concentration of lysate, the incubation time and temperature, the determination can be made sensitive to $10^4$ gram negative bacteria per milliliter of a urine sample without detecting the normal background bacteria level or $10^3$. To obtain meaningful results for $10^4$ cells, a clean catch mid- stream urine sample should be used.

1. Test Tube a. The Lysate

The lysate can be obtained in a lyophilized form from Associates of Cape Cod. The amount of lysate in the test tube must be high enough to provide a concentration of about 3.5 to 7 milligrams lysate per milliliter of test tube mixture formed after the sample is added to the test tube.

b. Divalent Cation

A divalent cation is required for the activation of the lysate cascade. Commercially available lysate preparations contain calcium ion as a stabilizer in sufficient amount to activate the lysate. Optionally, it may be desirable to add additional cation. The divalent cation can be chosen from the cations of calcium, magnesium, strontium and manganese; the cation of calcium is preferred. If a cation-free lysate preparation is used, divalent cation should be added.

c. First Buffer

The first buffer should be capable of resisting a pH change in the pH range of from about pH 6.3 to 7.5. Sodium or potassium phosphate can be used to prepare a preferred first buffer for the activation step. Choice of such a suitable first buffer is within the skill of the art given in this disclosure.

2. Test Device for the Test Tube/Test Device Method

The test device is composed of a carrier matrix incorporated with a synthetic peptide substrate containing a chromogenic or fluorogenic leaving group capable of being cleaved by the activated lysate, a second buffer capable of resisting a pH change in the pH range of from about 8.0 to about 8.9 when contacted by the test tube mixture. Optionally, an acidic polymer capable of stabilizing the cleaved group and/or a divalent cation group can be incorporated.

a. Carrier Matrix

The carrier matrix can be any substance capable of being incorporated with requisite components as long as it is substantially inert with respect to those components, porous and/or absorbent relative to the urine sample. The expression "carrier matrix" refers to either bibulous or nonbibulous matrices which are insoluble in and maintain their structural integrity when exposed to water or to other physiological fluids. A preferred carrier matrix is paper, usually high grade filter paper such as those available from Whatman, Clifton, N.J.

Incorporation can be accomplished by any method such as dipping, spreading or spraying which allows the carrier matrix to be incorporated with the substrate and the second buffer. This can be accomplished by impregnating a paper carrier matrix with an aqueous solution containing the substrate and second buffer and drying. Drying can be accomplished by any means which will not deleteriously affect the incorporated composition, usually by means of an air oven. The dried paper can thereafter be cut and mounted on one end of a support member, for example, a rigid or semirigid polystyrene film strip. Mounting of the paper on the polystyrene can be accomplished through use of double-faced adhesive tape such as those commercially available from the 3M Co., St. Paul, Minn. The support member provides a convenient handle which facilitates use of the test.

b. Synthetic Substrate

Although the formation of the natural cascade endpoint, gelation, has been used to detect bacteruria, quantitative results can then only be obtained by the use of expensive equipment which measures light scattering. The expense of this equipment makes the presently available test methods unsuitable for routine screening. In addition, the sensitivity of the light scattering methods has been reported as $10^5$ cells per milliliter.

It is more desirable to use a synthetic substrate which can provide an easily distinguishable colorimetric or fluorometric endpoint. A number of chromogenic or fluorogenic LAL substrates are being marketed for endotoxin LAL assays and can be used with the screening method provided by this invention.

Fluorogenic substrates for LAL are available from Peninsula Labs, Belmont, Ca., which contain N-methylcoumarin as a leaving group. These can be used with urine samples since the natural fluorescent background of urine is too low to cause significant interference with the required sensitivity of the test.

Chromogenic synthetic substrates are particularly preferred, since color can be determined either with relatively simple inexpensive instrumentation or, even more conveniently, visually by comparison to suitable color charts provided to the user. The only chromogenic substrates commercially available contain p-nitroaniline as a leaving group which produces a yellow color when cleaved by the activated lysate. Surprisingly, in spite of the yellow endpoint produced, these p-nitroaniline containing substrates have been successfully used to achieve the desired sensitivity with a urine specimen in the test tube/test device format. However, since clinical urines can be highly colored, e.g., high specific gravity urines, use of synthetic substrates capable of generating some color other than yellow is preferred.

Useful chromogenic substrates have a general formula:

B-(A$_1$)$_n$-A$_2$-Gly-Arg-I wherein
   (a) n is the integer zero or one;
   (b) A$_1$ is valine or leucine;
   (c) A$_2$ is leucine or serine;
   (d) Gly is glycine;
   (e) Arg is arginine;
   (f) B is a blocking group for the terminal amino acid; and
   (g) I is a chromogenic indicator group.

The blocking groups t-butyloxycarbonyl, acetyl, benzoyl or tosyl are preferred, with t-butyloxycarbonyl (tBOC) being especially preferred. Other equivalent amino acid sequences can be used, but generally those with a glycine-arginine sequence adjacent to the cleavable leaving group are preferred.

The preferred chromogenic indicator groups, are those where I, is chosen from I$_1$ or I$_2$, having the formulae:

(I$_1$)

(I$_2$)

wherein
   (a) Y is a hydroxyl or amido group;
   (b) X is chosen from sulfur, nitrogen or oxygen;
   (c) R$_1$ is a lower alkyl, aryl, amido or cyano group; and
   (d) R$_2$ can be single or multiple substituents, same or different, such as hydrogen, lower alkyl, aryl or, preferably, electron withdrawing groups such as chloro, nitro and the like.

The indicator group is linked to arginine through Y to form an amide or ester bond which can be cleaved by the action of the clotting enzyme formed with activation of the lysate.

Lower alkyl groups are alkyl groups containing from 1 to 4 carbon atoms. Included in the meaning of lower alkyl are methyl, ethyl, n-propyl, isopropyl, n-butyl, sec-butyl and tert-butyl groups. The groups can be substituted or not, provided the substitutions not interfere with the enzymatic cleavage of the amide or ester linkage.

The term "aryl" has the normal meaning well known to synthetic organic chemists, that is, an organic radical derived from an aromatic hydrocarbon by removal of one atom, for example phenyl from benzene. Such a substituent can also be substituted or unsubstituted provided that any substituents not interfere with the enzymatic cleavage of the ester or amide linkage by the clotting enzyme. These substrates are generally substrates for arginine specific proteases. However, the concentration of such proteases in urine is so low that it does not interfere with the sensitivity of the test for bacteruria.

A particularly preferred chromogenic substrate is wherein the indicator group I and the linking group, Y, form 3-aminoindole.

When the 3-aminoindole substrate is used, a coupling component must be incorporated into the test device to provide a colorimetric response. Suitable coupling components are diazonium compounds such as 2-methoxy-4-morpholinobenzene diazonium chloride, 2,4-dichlorobenzenediazonium, 2,6-dichlorobenzene diazonium, 5-chloro-2-methoxybenzene diazonium (Fast Red RC) and 2,3'-dimethylazobenzene diazonium (Fast garnet GBC). The diazo salt 2-methoxy-4-morpholinobenzene diazonium chloride (MMBD) is preferred. The test device so prepared and used with the method of this invention turned pink when the urine sample contacted contained 10$^4$ bacteria cells per milliliter. A wine color was seen when the bacteria concentration was 10$^6$ cells per milliliter.

d. Second Buffer

The second buffer must be capable of resisting a pH change in the pH range of from about 8.0 to 8.9 A preferred buffer is tris(hydroxymethyl)aminomethane (commonly known as TRIS).

e. Acidic Polymer

In order to obtain a color stable test using the test tube/test device method, an acidic polymer capable of stabilizing the cleaved leaving group can be incorporated with the carrier matrix. Suitable compounds include compounds such as methylvinyl ether and maleic acid available under the trademark GANTREZ® from GAF, New York, N.Y. When the preferred 3-aminoindole substrate is used with a diazonium salt in a paper carrier pretreated with GANTREZ®, a purple endpoint is obtained which is stable for a period of days.

f. Divalent Cation

Optionally, additional divalent cation can be incorporated with the carrier. Similar cations as used with the lysate activation step can also be used at this point. Calcium ion is preferred.

3. Use

An aliquot of a clean catch midstream urine sample is added to the test tube containing, a first buffer and sufficient lysate to produce a final concentration of about 3.5 to about 7 milligrams per milliliter of the test tube mixture formed. The test tube mixture is incubated for a time sufficient to activate the lysate; and the test device, incorporated as previously described, is contacted with the incubated mixture. The contacted test device is removed and the concentration of cleaved leaving group is determined either visually or instrumentally. Normal sterile procedures are used but no sample pretreatment is necessary.

The activation time required will depend on the test sensitivity desired. A test sensitive to 10$^4$ bacteria per milliliter sample will require a longer incubation time than a test sensitive only to 10$^5$ bacteria. However, the activation time must not be so long as to allow sensitivity to background contamination. Activation will occur more rapidly at elevated temperatures than at room temperature. For example, using a lysate obtained from Associates of Cape Cod, incubation for 15 minutes at 37° C. or 45 minutes at room temperature (25° C.) is required for activation to provide a test sensitive to $10^4$ E. coli per milliliter of undiluted urine. An assay sensitive to $10^5$ cells per milliliter of urine can be obtained with an incubation time of 30 minutes at 25° C. The determination of the time and temperature required to provide a desired sensitivity is within the ability of one skilled in the art given this disclosure.

The concentration of the cleaved leaving group can be determined in 2 to 5 minutes after contact of the test device with the activated test tube mixture. When the 3-aminoindole substrate and diazonium compound are incorporated into a carrier which was not pretreated with a stabilizer for the 3-aminoindole leaving group, the color generated can be stabilized by dipping the reacted test device in a 25% solution (by volume) of acetic acid.

The test tube/test device format provides a test of greater sensitivity to the presence of gram negative bacteria in a urine sample than reported for tests available on the market. In addition, the test can be performed in less than one hour even if room temperature incubation is used.

B. Unitary Solid State Test Device

A solid state unitary test device can be prepared with a synthetic substrate for the LAL assay which provides the same sensitivity to bacteruria ($10^5$ cells per milliliter of urine) as presently available methods using the LAL gelation assay and requiring expensive equipment. The unitary test device is composed of a carrier matrix incorporated with a test composition composed of lysate, a divalent cation, a synthetic substrate, a buffer component and a lysate stabilizing component. The unitary test device format provides a quick, convenient, inexpensive test especially suitable for screening large populations.

The carrier matrix can be any of those described previously as long as it is capable of holding sufficient reagents, particularly lysate, to provide a test of the desired sensitivity. Bibulous matrices, particularly paper, are preferred. Incorporation and drying of the matrix can be accomplished in any manner as described previously. A concentration of the lysate in the incorporating solution of approximately 15 milligrams per milliliter (mg/ml) is preferred. A particularly interesting aspect of a unitary test device using a paper matrix is that it does not respond to the presence of free endotoxin, but is sensitive to the presence of $10^5$ gram negative bacteria per milliliter of urine. This anomaly highlights the difficulty in transfering the presently available endotoxin assay formats to a unitary solid state test device format.

The lysate, divalent cation and synthetic substrates have been described previously. Preferred synthetic substrates are the commercially available ones disclosed previously with p-nitroaniline as the leaving group. To provide a unitary test device, a buffer component capable of resisting a pH change in the pH range from about pH 7.5 to about pH 8.5, preferably 7.5 to 8.0, is incorporated. Tris(hydroxymethyl)aminomethane is a preferred buffer component.

In addition to the test components noted above, when all the components required for an LAL chromogenic test are incorporated onto a carrier matrix such as paper, it is necessary to add a stabilizing agent which will stabilize the proenzymes in the lysate. This stabilizing component can be a neutral or negatively charged polymer and can be chosen from gelatin, interpolymers of methylvinyl ether and maleic anhydride, or polymers of ethylene glycol and isooctylphenyl ether. The interpolymers can be depicted by the structure:

where R is $C_1$–$C_{18}$ alkyl, ether, acetate or benzyl and n is an integer from 2 to the total number of repeating units of polymer. A preferred interpolymer is poly(methylvinylethoxymaleic anhydride), available from GAF, New York, N. Y. as Gantrez ®. Polyethylene glycol-p-isooctyl phenyl ether can be depicted by the structure:

A preferred polyethylene glycol-p-isooctylphenyl ether is available as Triton ® X-100 from Rohm & Haas, Philadelphia, PA. The stabilizing component is preferably incorporated with the paper matrix prior to incorporation of the lysate.

In use the unitary test device is dipped into an undiluted urine sample. The unitary device is then incubated at 37° C. in a closed chamber for 15 to 20 minutes, preferably with a negative control. As indicated previously the duration and temperature of incubation can be varied. However, a temperature of 37° C. is preferred over a lower temperature, for example 25° C. Any degree of color greater than that in the control denotes a positive sample. Color can be stabilized for later reading by dipping the strip in 25 or 50% (by volume) acetic acid. Normal sterile procedures are used, but no pretreatment of the sample is required. The sample should be a clean catch midstream urine sample. The unitary test device does not respond to free endotoxin in an aqueous solution, although it functions to distinguish the presence of $10^5$ bacteria from a negative sample.

The following examples describe experiments which were performed. While the examples serve to illustrate the invention they are not to be interpreted as limiting its scope, which is defined solely by the claims. One skilled in the art will be able to make such variations, substitutions and changes in the components of the composition and reaction parameters as may seem desirable.

V. Examples

The following abbreviations are used:

| | |
|---|---|
| g | gram |
| mmol | millimoles |
| mM | millimolar |
| mL | milliliters |
| μL | microliters |
| °C. | degrees centigrade |
| mp | melting point |
| t-BOC | tert-butyloxycarbonyl |

| | |
|---|---|
| DMF | dimethylformamide |
| Arg | arginine |
| Leu | leucine |
| Gly | glycine |
| L- | levorotatory |
| MS | mass spectrometry |
| FAB | fast atom bombardment (for MS) |
| $[\alpha]^{22}_D$ | optical rotation at 22° C. at wavelength of D line of sodium 5898 angstroms |
| CBz | carbobenzyloxy |
| psi | pounds per square inch (1 psi is equivalent to a pressure of 0.0704 kilogram per cubic centimeter) |

1. Preparation of Standards

E. coli slants were obtained from the Quality Assurance Department of Ames Division, Miles Laboratories, Inc. Nutrient broth, 10 mL, was inoculated with E. coli and incubated at 37° C. for 16 to 18 hours. This growth time usually produces approximately $10^{10}$ E. coli per milliliter stock broth. Actual E. coli concentration was determined by diluting the broth 7 and 8 fold and streaking 100 μL of each dilution on blood agar plates. Since each organism produces one colony, the number of organisms in 100 μL of dilution is obtained by counting the colonies which appear on the agar after overnight incubation at 37° C.

The quantitated stock broth was used to make appropriate E. coli dilutions for the LAL assay and was used within one week. This procedure assured a consistent amount of free endotoxin in the stock broth from shedding during growth and/or cell death.

2. Preparation Of Preferred Chromogenic Substrate

All amino acids used in the synthesis had the levorotatory configuration.

3-AMINOINDOLE (I)

A 250 ml round-bottomed flask equipped with a condenser, a drying tube and an additional funnel was flushed with argon for 15 minutes. Then sodium (1.3 g, 57 mmol, freshly cut into small pieces) and 10 μL of anhydrous ethanol were placed in the round flask, followed by dropwise addition of 9 mL of anhydrous ethanol. When the addition of anhydrous ethanol was complete and the gentle reflux of the reaction mixture had subsided, the reaction mixture was heated to gentle reflux for 15 minutes. Then the heating source was removed and indole (5 g, 45 mmol) was added. The reaction mixture was stirred until all indole dissolved. Isoamylnitrite (12 mL, 89 mmol), which was dried over anhydrous potassium carbonate before use, was added dropwise over a period of 30 minutes. The reaction mixture was stirred at room temperature under argon overnight.

The reaction mixture was concentrated to remove alcohol and distilled water (100 mL) was added. The resulting mixture was heated to boiling. Under argon, a solution of potassium hydroxide (30 g, 540 mmol) and sodium dithionite (23 g, 132 mmol) in 125 mL of distilled water was added dropwise. Dark green solid began to separate out and the solution turned a lighter color and finally became yellow. After the addition of the potassium hydroxide/sodium dithionite solution, 100 mL distilled water was added and the reaction mixture was heated to boiling for 10 minutes. The dark green solid was filtered off from the hot solution under argon. Yellow crystals in plate form separated out from the yellow filtrate on cooling under argon. The yellow crystals were collected and recrystallized from hot water to yield light beige needle crystals, I, 2.7 g (48% yield), mp. 120° C. (turned dark), MS(FAB, M+ =132, 100%).

t-BOC-L-Leu-gly, (II)

Under argon, a solution of t-BOC-L-Leucine (5 g, 20 mmol) and N-hydroxy succinimide (2.3 g, 20 mmol) in 25 moles of anhydrous dimethylformamide was cooled in an ice-bath. Dicyclohexylcarbodiimide (4.5 g, 22 mmol) was added and the reaction mixture was stirred in an ice-bath for 3 hours. A solution of glycine (1.5 g, 20 mmol) and sodium bicarbonate (3.4 g; 400 mmol) in 48 mL of distilled water was added and the resulting mixture was allowed to warm up to room temperature slowly and was stirred overnight. The white solid separated out, was filtered off and the filtrate was adjusted to pH 3 with 6 Normal hydrochloric acid. The solution was then extracted twice with ethylacetate. The ethylacetate extract was dried over anhydrous magnesium sulfate and concentrated first on a rotatory evaporator and then under high vacuum. The concentrate produced 8 g of oil residue. After flash chromatography using 170 g of silica gel and $CH_2Cl_2/CH_3OH/NH_4OH$ (80:20:2 by volume) as the eluting solvent, 2.73 g of white solid of t-BOC-L-Leu-Gly ammonium salt was obtained. About 2.3 g of the ammonium salt was dissolved in 20 mL of distilled water and the solution was adjusted to pH 3 with 6 Normal hydrochloric acid. The free acid was extracted with ethylacetate twice (total 100 mL). The ethylacetate solution was dried over magnesium sulfate, concentrated and produced 2.1 g of white solid, II mp 116°-117.5° C., MS(FAB, M+1=289), $[\alpha]^{22}_D$= −28.2° (C=1.15, $CH_3OH$), Analysis Calculated for $C_{13}H_{24}N_2O_5$: C, 54.15; H, 8.39; N, 9.71. Found: C, 54.26; H, 8.37; N, 9.62.

$N_\alpha$-CBz-$N_\omega$-nitro-L-Arg-3-Indolylamide (III)

Under argon, a solution of $N_\alpha$CBz-$N_\omega$-nitro-L-arginine (13.4 g, 37.8 mmol) and triethylamine (5.3 mL 37.8 mmol) in 82 mL of anhydrous dimethylformamide was cooled to −20° C. in a methanol-dry ice bath. Isobutylchloroformate (5 mL, 37.8 mmol) was added and the reaction mixture was stirred at −20° C. for 45 minutes. Then 3-aminoindole (2.80 g, 21.2 mmol) was added and the resulting mixture was allowed to warm up to room temperature slowly and was stirred overnight. Distilled water was added to the reaction mixture and 5% sodium bicarbonate was added until pH 9 was reached. The solution was then extracted with ethylacetate (250 mL) twice. The ethylacetate extract was dried over anhydrous magnesium sulfate and concentrated to give a light brownish green oil residue. The oil was subjected to flash chromatography with 170 g of silica gel and $CH_2Cl_2/CH_3OH$ (95:5, by volume) as eluting solvent. Recrystallization from $CH_2Cl_2/CH_3OH$ yielded 5.18 g (53%) of white crystals, III, mp. 202°-203° C., MS(FAB, M+1=468), $[\alpha]^{22}_D$=+13.1 (C=1.08, DMF).

Analysis Calculated for $C_{22}H_{25}N_7O_5$: C=56.52; H, 5.39; N, 20.97. Found: C=56.32; H, 5.40; N, 20.77.

L-Arg-3-indolylamide . 2HOAc, (IV)

$N_\alpha$-CBz-$N_\omega$-nitro-L-Arg-3-indolylamide (0.93 g; 20 mmol) was dissolved in 25 mL of anhydrous ethanol and 25 mL of glacial acetic acid with gentle heating to give a light yellow solution. Then 10% palladium in carbon (Pd/C, 500 mg) was added and the mixture was hydrogenated under 50 psi (3.52 kilograms per cubic centimeter) of hydrogen gas for 15 hours. The mixture was filtered and the filtrate was concentrated to give a light green oil residue. After flash chromatography with 63 g of silica gel and $CH_2Cl_2/CH_3OH$ (1:1, by volume) as the eluting solvent, 300 mg of light brown solid of IV was obtained. (37% yield). MS(FAB, M+1=289).

Anal. Calcd. for $C_{14}H_{20}N_6O.2HOAc.3H_2O$: C:46.75; H:7.41; N:18.17.

Found:C:46.73; H:7.12; N:17.93.

t-BOC-L-Leu-Gly-L-Arg-3-indolylamide, (V)

Under argon, a solution of t-BOC-L-Leu-glycine (158 mg, 0.55 mmol) and triethylamine (0.077 mL, 0.55 mmol) in 1.6 mL of anhydrous dimethylformamide was cooled to $-20°$ C. in a methanol-dry ice bath. Isobutylchloroformate (0.070 mL, 0.55 mmol) was added and the resulting reaction mixture was stirred at $-20°$ C. for 25 minutes. A solution of L-Arg-3-indolylamide.2-HOAc (200 mg. 0.49 mmol) and triethylamine (0.070 mL, 0.49 mmol) in 1.1 mL of anhydrous dimethylformamide was added and the resulting reaction mixture was allowed to warm up to room temperature slowly and stirred overnight. Distilled water was added to the reaction mixture and the solution was adjusted to pH 7.2 with 5% sodium hydroxide. The solution was then concentrated to give an oil residue which after flash chromatography using $CH_2Cl_2/CH_3OH/NH_4OH$ (80:20:5, by volume) as the eluting solvent and recrystallized from $CH_3OH/H_2O$, gave 200 mg of white solid, V. (67% yield) m.p. 125° C. (soften), MS(FAB, M+1=559), $[\alpha]_D^{22} = -25.2°(C=1.06, CH_3OH)$; High resolution mass spectrum, (positive ion mode) Calculated for $C_{27}H_{42}N_8O_5+1=559.33559$. Found:=559.33563.

3. Test Tube/Test Device Format

A test tube suitable for use in the test tube/test device method with 100 microliter urine sample was prepared by adding 50 μL of 100 mM phosphate buffer and 1.7 milligrams lysate obtained from the Associates of Cape Cod, Woods Hole, MA. to the test tube. Whatman 31 ET paper was dipped in a 2% (w/w) aqueous solution of Gantrez AN-119 obtained from GAF, New York, N.Y. buffered between pH 8 and 9 with Tris(hydroxymethyl)aminomethane. The paper was then dried in an air oven at 50° C. for 10 minutes. The dried pretreated paper was dipped in a solution, buffered at pH 8.7, containing 10 mM calcium ion, 1 mM indole substrate (V) and 0.24 mM 2-methoxy-4-morpholinobenzene diazonium chloride. The doubly incorporated paper was again dried at 50° C.

Figure 1:
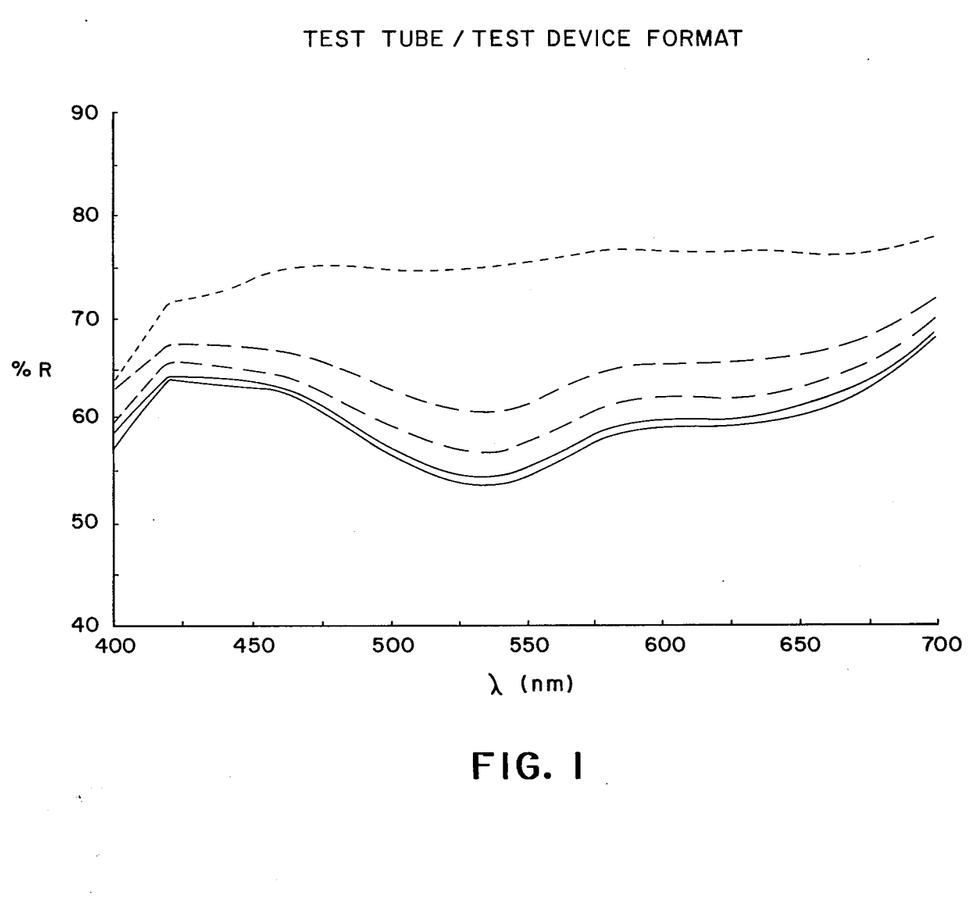
FIG. 1 is a graph showing data collected with the test tube/test device method of the present invention. The test device was prepared with a chromogenic LAL substrate containing 3-aminoindole as a leaving group and a color stabilizing polymer. The graph is a computer plot of percent reflectance, %R, versus wavelength, $\lambda$. The color development of the test device was monitored every forty five seconds after contact with a test tube mixture prepared with a negative urine sample spiked to contain $10^4$ cells of E. coli per milliliter.

A 100 μL aliquot of a clean catch urine sample was placed into the test tube and the test tube mixture formed was incubated at 37° C. for 15 minutes. The test device, formed by affixing a piece of the doubly dried and impregnated paper onto a plastic support as handle, was dipped into the incubated test tube mixture and removed. Two minutes after contact with the mixture, the color development of the reacted test device was read. Results are shown graphically in FIG. 1. The format can detect $10^4$ cells per milliliter. The test device was darker shades of purple as the E. coli concentration is increased to $10^6$ cells per milliliter. Color development essentially stopped after approximately 2 minutes. Comparable results were obtained when the test tube mixture was incubated at 25° C. (room temperature) for 45 minutes. Comparable sensitivity ($10^4$) was obtained with Eaton and Dikeman 205 paper as the carrier.

4. Unitary Solid State Test Device

A unitary solid state test device sensitive to the presence of at least $10^5$ cells per milliliter of urine was prepared as follows. Eaton and Dikeman 205 paper was dipped in a 2 percent solution of GANTREZ® AN 119 obtained from GAF, New York, N.Y. adjusted to a pH of about 7.5 with sodium hydroxide. The pretreated paper was dried at 50° C. for at least 10 minutes. A lysate solution was prepared by reconstituting lysate (Pyrotell obtained from Associates of Cape Cod) in an aqueous solution buffered at about pH 7.8 with 50 mM Tris buffer. The solution also contained approximately 1.1 mM Spectrozyme LAL substrate from American Diagnostica, Greenwich, CT. Spectroenzyme is a tripeptide with p-nitroaniline as the leaving group (acetyl-D-hexahydrotyrosine-glycine-argine-p-nitroaniline). The Pyrotell preparation contains calcium ion and other stabilizers.

Figure 2:
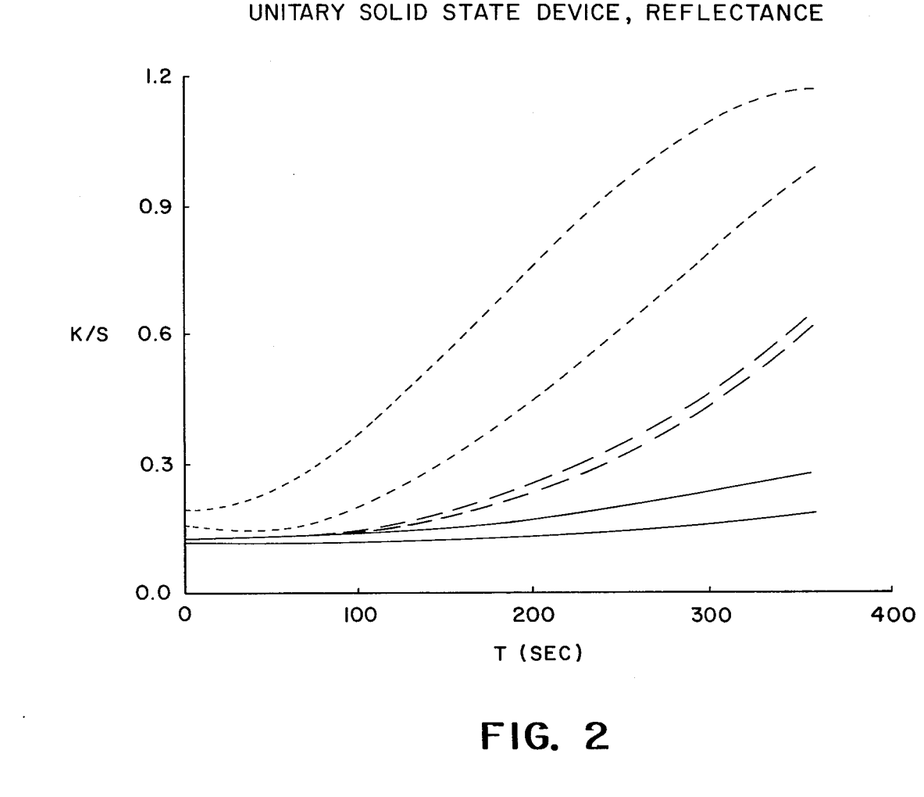

The dried pretreated paper was dipped in the lysate solution and dried again at 50° C. for about 10 minutes. The doubly dried and incorporated paper was cut into small oblongs and affixed to a polystyrene support with a double sided adhesive. The device was contacted with a urine sample, removed, incubated at 37° C. for approximately 15 minutes and a reflectance reading was taken. The results shown in FIG. 2 indicate the ability of the unitary test device to distinguish $10^5$ cells per milliliter from a negative sample. Similar results have been obtained with the Mallinkrodt substrate in the Color Lysate Chemistry kit.

Experimental attempts to use the test device with solutions containing only free endotoxin showed the unitary test device is not sensitive to free endotoxin.

Obviously, many modifications and variations of the invention as set forth may be made without departing from the spirit or scope of the invention.

What is claimed is:

1. A gram negative bacteria screening method for determining the presence of at least $10^4$ gram negative bacteria cells per milliliter of a urine sample, comprising the steps of:

(a) adding an undiluted urine sample to be tested to a test tube containing horseshoe crab amebocyte lysate and a first buffer capable of resisting a pH change in the pH range of from about 6.3 to about 7.5, to form a test tube mixture wherein the concentration of lysate is at least 3.5 milligrams per milliliter of the test tube mixture formed;

(b) incubating the test tube mixture for a time sufficient to activate the lysate;

(c) contacting a test device with the activated test tube mixture, said test device comprising a carrier matrix incorporated with a synthetic peptide substrate containing a chromogenic or fluorogenic leaving group capable of being cleaved by the activated lysate and a second buffer capable of resisting pH change in the pH range of from about 8.0 to about 8.9;

(d) removing the contacted test device; and (e) determining the concentration of cleaved leaving group.

2. The screening method of claim 1 in which the lysate is Limulus amebocyte lysate.

3. The screening method of claim 1 in which the carrier matrix is additionally incorporated with a divalent cation.

4. The screening method of claim 1 in which divalent cation is additionally added to the test tube prior to incubation.

5. The screening method of claim 3 in which the divalent cation is selected from the group consisting of calcium, magnesium, strontium and manganese.

6. The screening method of claim 5 in which the divalent cation is calcium.

7. The screening method of claim 1 in which the leaving group is chromogenic.

8. The screening method of claim 1 in which the chromogenic leaving group is 3-aminoindole and the carrier matrix is additionally incorporated with a diazonium salt.

9. The screening method of claim 8 in which the carrier matrix is pretreated with an interpolymer of methylvinyl ether and maleic anhydride.

10. A unitary gram negative bacteruria screening device for determining the presence of at least $10^5$ gram negative bacteria per milliliter of a urine sample, comprising:
 (a) a carrier matrix; and
 (b) a test composition incorporated with the carrier matrix, which composition includes horseshoe crab amebocyte lysate, a divalent cation, a synthetic peptide substrate with a chromogenic or fluorogenic leaving group capable of being cleaved by the lysate, a buffer component capable of resisting a pH change in a pH range of from about 7.5 to about 8.5 and a stabilizing component capable of stabilizing the lysate.

11. The unitary screening device of claim 10 in which the lysate is *Limulus amebocyte* lysate.

12. The unitary screening device of claim 10 in which the leaving group is chromogenic.

13. The unitary screening device of claim 10 in which the divalent cation is selected from the group consisting of calcium, magnesium, strontium and manganese.

14. The unitary screening device of claim 10 in which the stabilizing component is a member selected from the group consisting of gelatin, interpolymers, of methylvinyl ether and maleic anhydride and polyethylene glycol p-isooctylphenyl ether.

15. The unitary screening device of claim 12 in which the chromogenic leaving group is p-nitroaniline.

16. A method for preparing a unitary gram negative bacteruria unitary test device for determining the presence of at least $10^5$ gram negative bacteria per milliliter of a urine sample, comprising the steps of:
 (a) incorporating a carrier matrix with a stabilizing component capable of stabilizing horseshoe crab amebocyte lysate;
 (b) drying; and
 (c) incorporating the dried matrix with a test composition including horseshoe crab amebocyte lysate, a divalent cation, a synthetic peptide substrate with a chromogenic or fluorogenic leaving group capable of being cleaved by the lysate and a buffer component capable of resisting a pH change in a pH range of from about 7.5 to about 8.5; and
 (d) drying.

* * * * *